(12) United States Patent
Habeb et al.

(10) Patent No.: US 11,337,773 B2
(45) Date of Patent: May 24, 2022

(54) DENTAL APPARATUS

(71) Applicant: EMUDENT TECHNOLOGIES PTY LTD, Hornsby (AU)

(72) Inventors: Alaa Habeb, Hornsby (AU); Omar Zuaiter, Hornsby (AU)

(73) Assignee: EMUDENT TECHNOLOGIES PTY LTD, Hornsby (AU)

( * ) Notice: Subject to any disclaimer, the term of this patent is extended or adjusted under 35 U.S.C. 154(b) by 0 days.

(21) Appl. No.: 16/060,931

(22) PCT Filed: Nov. 25, 2016

(86) PCT No.: PCT/AU2016/051157
§ 371 (c)(1),
(2) Date: Jun. 9, 2018

(87) PCT Pub. No.: WO2017/100828
PCT Pub. Date: Jun. 22, 2017

(65) Prior Publication Data
US 2018/0368936 A1    Dec. 27, 2018

(30) Foreign Application Priority Data

Dec. 15, 2015 (AU) ................................ 2015905180

(51) Int. Cl.
*A61C 1/08* (2006.01)
*A61C 3/02* (2006.01)
*A61B 5/00* (2006.01)
*A61C 1/00* (2006.01)

(52) U.S. Cl.
CPC ............ *A61C 1/082* (2013.01); *A61B 5/0088* (2013.01); *A61B 5/682* (2013.01); *A61C 1/0007* (2013.01); *A61C 3/02* (2013.01); *A61B 5/0071* (2013.01)

(58) Field of Classification Search
CPC ......... A61C 1/082; A61C 3/02; A61C 9/0046; A61C 1/0007; A61C 1/00; A61B 5/682; A61B 5/4547; A61B 5/0088
See application file for complete search history.

(56) References Cited

U.S. PATENT DOCUMENTS 2,675,616 A    4/1954    Dritz
3,839,797 A *  10/1974   Randolph .............. A61C 1/082
                                                      433/27
5,846,081 A    12/1998   Bushway
(Continued)

OTHER PUBLICATIONS

International Search Report for PCT/AU2016/051157, Completed by the Australian Patent Office dated Feb. 22, 2017, 4 Pages.
(Continued)

*Primary Examiner* — Heidi M Eide
*Assistant Examiner* — Drew S Folgmann
(74) *Attorney, Agent, or Firm* — Brooks Kushman P.C.

(57) ABSTRACT

An apparatus assisting in dental procedure, comprising: a body adapted to be received with an oral cavity; an anchoring means for securing the body within the oral cavity such that it at least partially surrounds one or more teeth; a dental device located within the body and adapted to move in a plurality of planes relative to the one or more teeth; and a controller for controlling the dental device to move into a suitable position relative to the one or more teeth and once located in position carry out work on or about the one or more teeth.

9 Claims, 6 Drawing Sheets

(56) References Cited

U.S. PATENT DOCUMENTS

| | | |
|---|---|---|
| 6,201,880 B1 | 3/2001 | Elbaum |
| 2005/0084816 A1 | 4/2005 | Mehdizadeh |
| 2008/0176187 A1 | 7/2008 | Stumpel |
| 2011/0143307 A1 | 6/2011 | Takebayashi |
| 2011/0316994 A1* | 12/2011 | Lemchen ............... H04N 5/232 348/66 |
| 2014/0339392 A1* | 11/2014 | Enokijima ........... B60N 2/0232 248/429 |
| 2015/0140507 A1 | 5/2015 | Moffson et al. |
| 2015/0173852 A1 | 6/2015 | Khakpour et al. |
| 2015/0182299 A1 | 7/2015 | Koubi et al. |
| 2016/0157964 A1* | 6/2016 | Suttin .................. A61C 8/0089 433/27 |

OTHER PUBLICATIONS

European Search Report for EP 168741193.7/ PCT/AU2016051157, Dated Nov. 4, 2019.

* cited by examiner

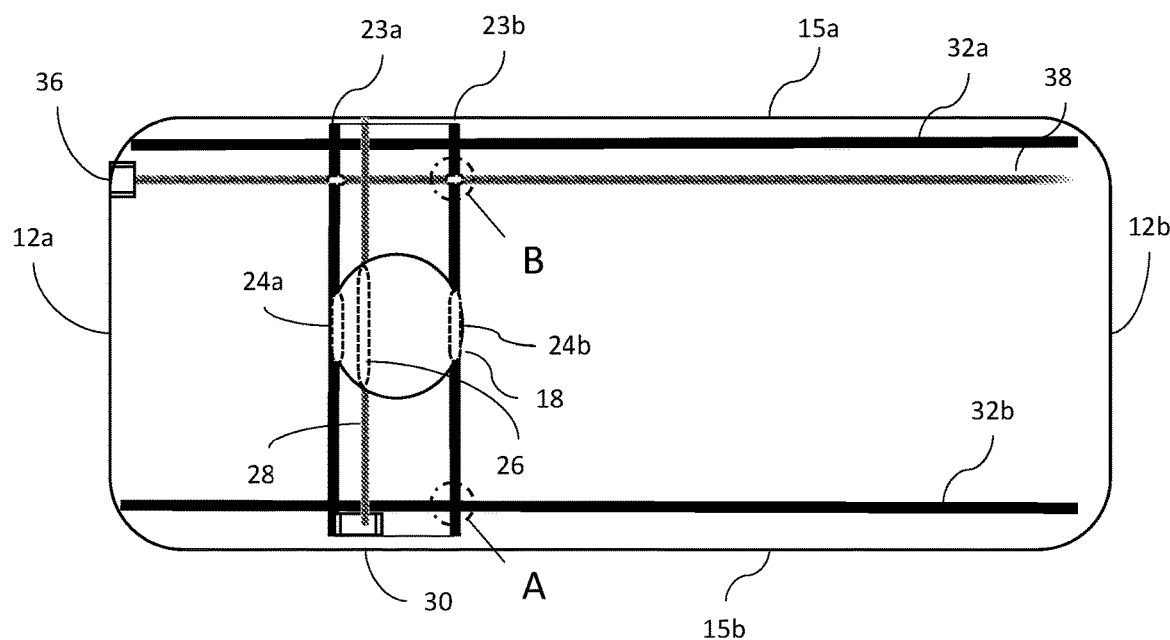
Figure 4a
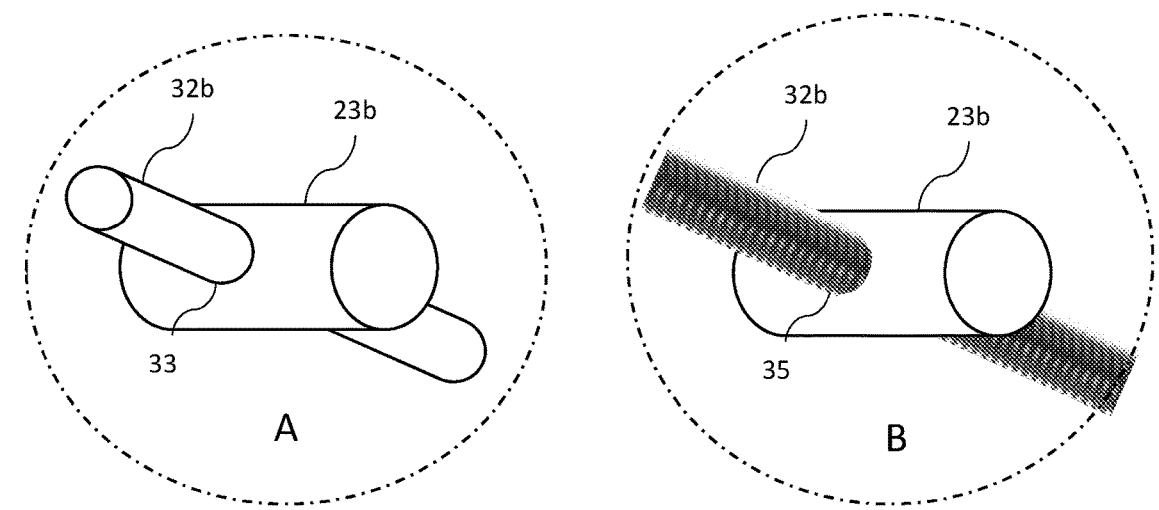
Figure 4b
Figure 4c

DENTAL APPARATUS

CROSS-REFERENCE TO RELATED APPLICATION

This application is the U.S. national phase of PCT Application No. PCT/AU2016/051157 filed on Nov. 25, 2016, which claims priority to AU Patent Application No. 2015905180 filed on Dec. 15, 2015, the disclosures of which are incorporated in their entirety by reference herein.

FIELD OF INVENTION

The present invention relates to an apparatus assisting in dental procedures.

BACKGROUND OF INVENTION

Since the inception of modern dentistry during the late nineteenth century, dental diagnosis and treatment has relied largely on the same techniques. For example, dentists have been using a handpiece encasing a rotary engine with an attached cutting bur to manually prepare a cavity within a tooth, or reduce it circumferentially to accommodate for a filling material, crown or a mix of both.

The same tenet applies to the diagnosis of tooth decay (dental caries), which is one of the most ubiquitous diseases in human populations. The importance of reaching a definite diagnosis cannot be overemphasized, as it will govern the choice of a consequent treatment modality, be it prevention, monitoring, operation (drilling) or extraction. Basically, diagnosis depends on the practitioner's clinical acuity, as carious lesions can prove to be elusive to assess particularly when asymptomatic, located in the morphologically complex pits and fissures, or when caries has not yet progressed to induce visible cavitation. Hidden caries, which advance deep under an otherwise apparently sound surface, is yet another challenging situation for the diagnostician.

Therefore, when faced by such circumstances, a dentist may resort to diagnostic aids such as radiographs, optical magnifiers, staining dyes, thermal tests, fluorescence or transillumination. However, their efficiency and effectiveness in dental settings are often compromised by technique sensitivity (radiographic reproducibility for example), increased cost, fear of radiation exposure, proper chronological archiving and retrieval of results, as well as the time and effort of using different standalone devices and systems which may also inconvenience the patient and staff.

In addition, the accessibility to a particular tooth may be a determining factor in diagnosis, planning and performing dental treatment. Plausibly, the more posterior a tooth is in the mouth, the less amenable it is for instrumentation and handling. Apart from accessibility, careful surgical precision must be maintained at all times throughout the drilling procedure, as the clinician is not only working within confined and miniscule structures, but he also ought to strictly avoid inadvertent damage to sound tissues around and within the tooth such as the delicate and centrally located pulp.

Consequently, the outcome of dental care remains technique, equipment and time sensitive, and thus quite vulnerable to human error, misjudgement and indexterity. This serves to limit the number of patients or teeth a practitioner can attend to, and accounts for steadily rising costs. This relative unimproved productivity of the healthcare professions (as compared to other fields that became more affordable and productive with industrial automation) has been described as the "Baumol Effect".

It would be advantageous if there was a way to improve and streamline the diagnosis process, enhance visibility and access, minimise human error, reduce manual effort and fatigue, and/or perform rapid, precise and ideal tooth preparation.

SUMMARY OF INVENTION

In accordance with a first aspect of the present invention there is provided an apparatus assisting in dental procedure, comprising: a body adapted to be received with an oral cavity; an anchoring means for securing the body within the oral cavity such that it at least partially surrounds one or more teeth; a dental device located within the body and adapted to move in a plurality of planes relative to the one or more teeth; and a controller for controlling the dental device to move into a suitable position relative to the one or more teeth and once located in position carry out work on or about the one or more teeth.

In an embodiment the body is adapted to be wholly received within the oral cavity.

In an embodiment the work performed by the dental device includes at least one pre-programed procedure.

In an embodiment the anchoring means is a clamp that is adapted to secure to the one or more teeth and/or a tooth or teeth adjacent to the one or more teeth.

In an embodiment the clamp comprises one or more clamp peaks and one or more clamp bows and wherein the body is coupled to the bow(s).

In an embodiment the body comprises one or more cameras operable to take an image of the work site and wherein the controller is configured to process the resultant image data for use in determining at least one of:
a. the position to locate the dental device for performing the work;
b. appropriate selection of the preprogramed procedure;
c. monitor in real time the operations performed by the apparatus; and
d. diagnose anomalies of the tooth structures by means of direct imagery, transillumination and/or fluorescence.

In an embodiment the dental device comprises one or more lights for illuminating the oral cavity.

In an embodiment the one or more lights are transillumination lights adapted to transilluminate the one or more teeth.

In an embodiment the controller comprises a processing unit programmed to instruct the work device to perform work.

In an embodiment the apparatus further comprises a conduit for supplying or expelling contents to the apparatus.

In an embodiment the contents are at least one of fluids, gases or solids.

In an embodiment the dental device is at least one of a mechanical bur, forceps, root elevators, scalpel, a mirror, a laser, a camera, an excavator, a dental burnisher, a dental plugger, a scaler, local anaesthetic vehicle, a curette or other dental instrument.

In an embodiment movement of the dental device in the at least three planes is caused by the dental device moving along one or more sets of rails.

In an embodiment at least one of the one or more sets of rails are adapted to move under the control of an actuator.

In an embodiment the apparatus further comprises a rotary motor within the body that can be either air, water, steam or electrically powered.

In accordance with a second aspect there is provided a method assisting in dental procedure, comprising utilising the dental apparatus according to any one of the preceding claims for performing the dental procedure.

In accordance with a third aspect there is provided a computer readable medium storing computer program code which, when executed by a computer processor, is operable to control the controller of claim 1 to operate the dental work device.

BRIEF DESCRIPTION OF DRAWINGS

Embodiments of the present invention will now be described, by way of example only, with reference to the accompanying drawings, in which:

FIG. 2b is a sectional view through C-C shown in FIG. 2a;

FIG. 4a is an internal view of the body of the FIG. 1 apparatus;

FIG. 4b is a close up view of feature A shown in FIG. 4a;

FIG. 4c is a close up view of feature B shown in FIG. 4a;

DETAILED DESCRIPTION

Figure 1:
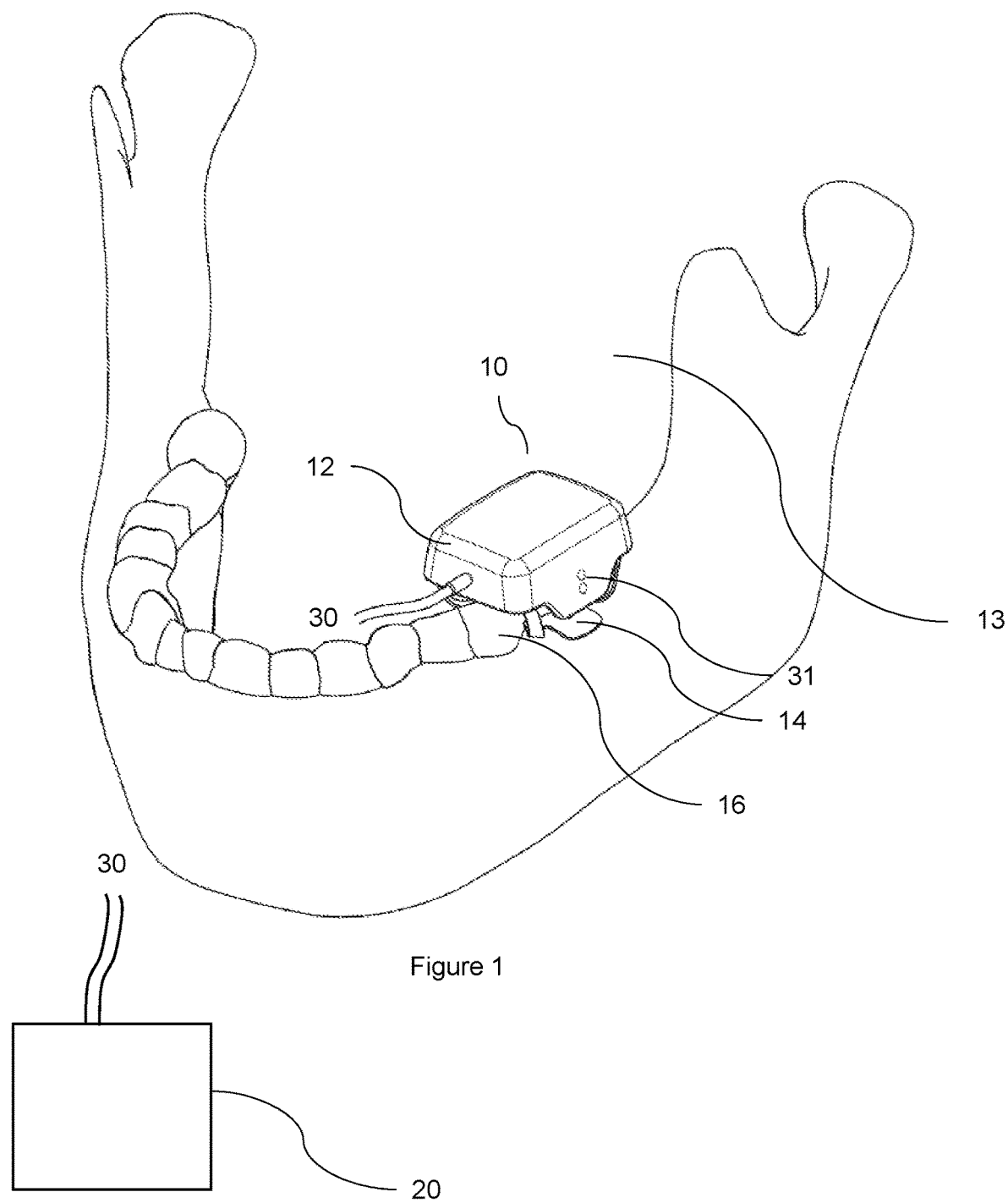
FIG. 1 is a schematic of an apparatus located within a patient's mouth, in accordance with an embodiment of the present invention.

Embodiments of the invention described herein relate to an apparatus for assisting in dental procedures. With reference to FIGS. 1 to 5, the apparatus 10 comprises a body 12 adapted to be received within an oral cavity 13 of a patient. The body 12 is secured within the oral cavity 13 via an anchoring means 14, such that the body 12 at least partially surrounds one or more teeth 16. A dental work device 18 (see particularly FIGS. 2 and 5) is movable within the body 12 and is adapted to move in a plurality of planes relative to the one or more teeth 16. A controller 20 is operable to cause the dental work device 18 to move into a desired position and thereafter actuate the dental work device 18 for carrying out work on or about the one or more teeth 16. The work performed by the apparatus 10 includes, but is not limited to, at least one of dental drilling, suction, imaging and illumination.

Configuration of the Apparatus

Figure 2C:
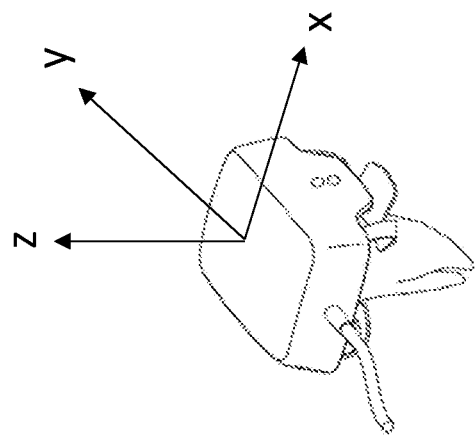
FIG. 2c is an isometric view of the apparatus.
Figure 2F:
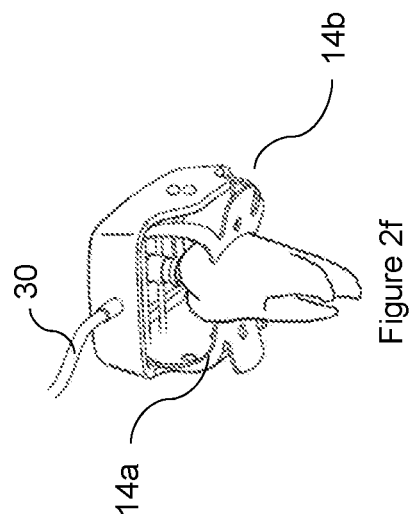
FIG. 2f is a further isometric view of the apparatus.
Figure 2B:
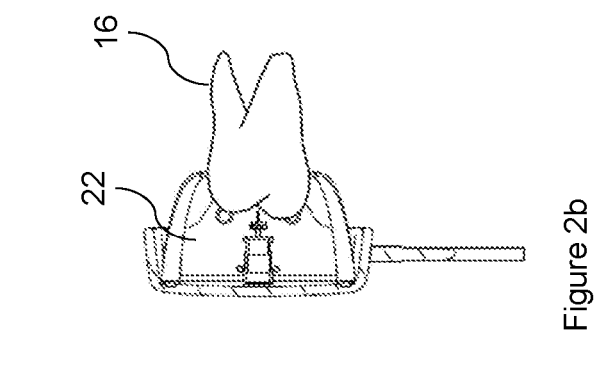
Figure 2E:
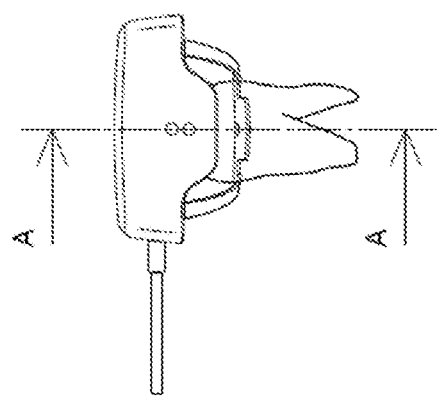
FIG. 2e is a side view of the apparatus.
Figure 2A:
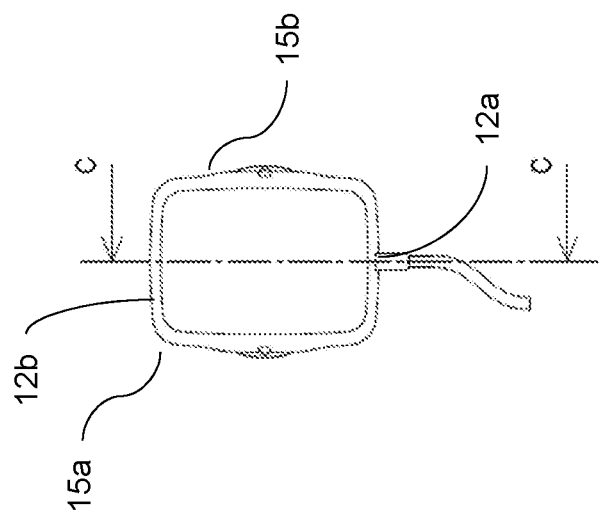
FIG. 2a is a top view of the apparatus of FIG. 1, anchored to a single tooth.
Figure 2D:
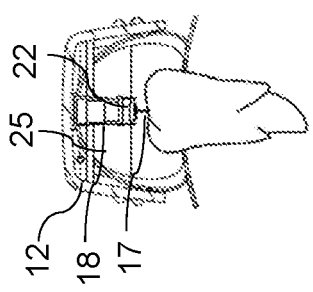
FIG. 2d is a section view through A-A shown in FIG. 2e.
Figure 3:
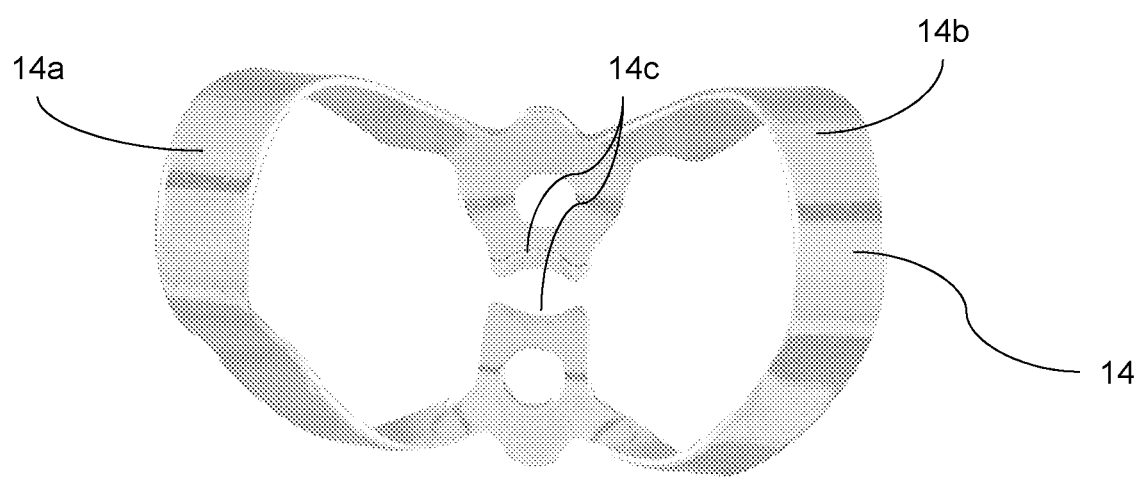
FIG. 3 is an isometric view of a clamp used for anchoring the apparatus, in accordance with an embodiment.

In more detail, and with particular reference to the elevation and section views depicted in FIG. 2, the body 12 of the apparatus 10 is generally rectangular in shape with chamfered edges for minimising patient discomfort. The body 12 may be formed from any suitable material, including plastic, metal, a suitable composite material or the like. The dental work device 18 is housed within the body 12 and includes an attachment 17 for use in carrying out the work. As previously stated, the apparatus 10 (and more particularly the body 12) is anchored within the oral cavity 13 via an anchoring means 14. According to the illustrated embodiment, the anchoring means 14 takes the form of a clamp 14 that secures to the crown of a single tooth 16. FIG. 3 shows the clamp 14 in isolation. With reference to both FIGS. 3 and 4, the clamp 14 comprises a pair of bows 14a, 14b that detachably couple respectively to ends 12a, 12b of the body 12. The bows 14a, 14b extend to opposing clamp beaks 14c that firmly secure to the crown of a tooth adjacent to the gingiva (i.e. in the same manner as existing dental clamps used by dentists to attach the rubber dam). According to the illustrated embodiment, the bows 14a, 14b attach to the body via moveable arms that firmly hook under the bows 14a, 14b and thereafter can be locked in place to prevent the body from detaching from the clamp 14. It will be understood that any suitable detaching means could be used for securing the clamp to the body 12 (e.g. frictional, magnetic or latch fit), depending on the desired implementation. For example, the bows 14a, 14b may include openings for receiving screws that screw into the body for securing the clamp thereto. In yet another alternative embodiment, the clamp 14 may be fixedly secured to the body, e.g. via an adhesive. In yet another alternative embodiment, the clamps may be integrally formed with the body 12 (e.g. set in place during forming of the body).

As previously mentioned, the apparatus 10 is adapted to perform work within a work site. According to the illustrated embodiment the work site comprises a tooth 16 (or teeth) that the body 12 at least partially surrounds. The dental work device 18 is moveable in three planes relative to the tooth 16, as depicted in FIG. 2c, for moving into a desired position. Furthermore, the dental work device 18 includes a rotator and pivot mechanism for allowing the attachment 17 to both rotate and pivot (i.e. in an additional two planes) once the dental work device 18 is located in a desired position.

In more detail, and with additional reference to FIG. 4a, there is shown a sectional view of the internal housing of the body 12 for illustrating movement of the dental work device 18 in the X and Y planes. As shown, a pair of rails 23a, 23b extend between side walls 15a, 15b of the body 12. The dental work device 18 couples to the rails 23a, 23b for sliding movement there along. According to the illustrated embodiment, the rails 23a, 23b are closely received in openings 24a, 24b (i.e. having an internal profile that corresponds to the sectional profile of the rails ensuring smooth sliding operation) that are disposed on opposite sides of a body 12 of the work device 18. A further opening 26 extends through the body 12 of the dental work device 18 for receiving a threaded lead screw 28 extending from an actuator in the form of a stepper motor 30. The further opening 26 has a threaded internal profile corresponding to the thread of the lead screw 28. Actuation of the stepper motor 30 (either in the forward or reverse direction) causes the dental work device 18 to move along the rails 23a, 23b thereby facilitating precision open-loop positioning of the device 18 in the X plane. Positioning along the Y plane is achieved by way of rails 32a, 32b which extend between ends 12a, 12b of the body 12 and fixed thereto. The rails 32a, 32b pass through openings 33 disposed in the rails 23a, 23b, as shown in the close-up view of FIG. 4a. A second actuator (also in the form of a stepper motor 36) controls a second lead screw 38 which passes through openings 35 disposed in rails 23a, 23b. An internal profile of the openings 35 has a corresponding thread to the second lead screw 38, thereby facilitating movement of the dental work device 18 in the Y plane as the stepper motor is actuated (again either in forward or reverse). The close up view of FIG. 4c shows this in more detail. It will be understood that other configurations could be utilised for achieving the sliding movement of the dental work device 18 in the X and Y planes, for example using tracks embedded in an internal wall of the body 18 that receive and retain rollers disposed on the work device 18 and which may be powered to move along the tracks for suitably positioning the work device. According to the illustrated embodiment, the dental work device 18 is adapted to move up to 2 cm in in the X and Y planes.

Figure 5A:
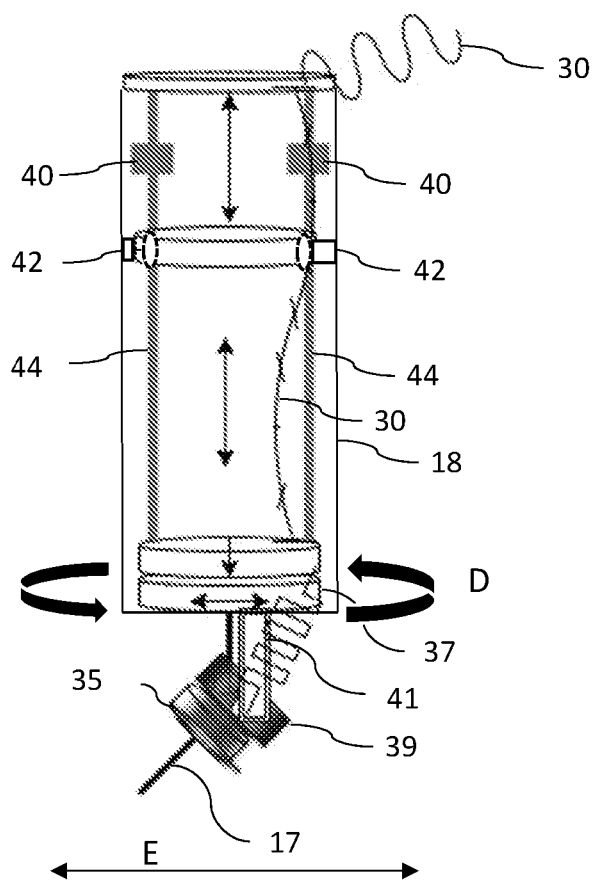
FIG. 5a is a schematic of a dental work device of the apparatus, in accordance with an embodiment.
Figure 5B:
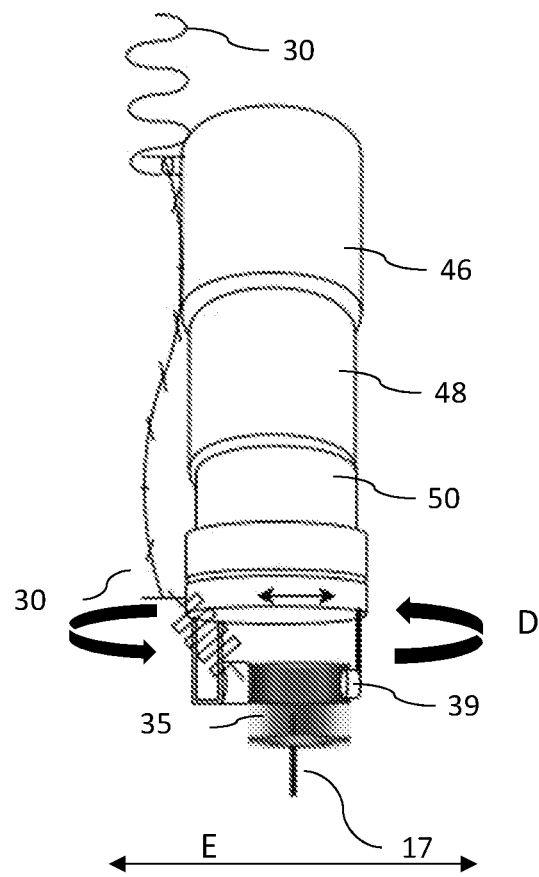
FIG. 5b is a schematic of a dental work device in accordance with an alternative embodiment.

Movement in the Z plane (i.e. for controlling the height of the dental work device attachment 17 relative to the tooth 16) is achieved by way of a third actuator. With reference to FIG. 5a, there is shown a schematic of the dental work device 18 whereby the third actuator takes the form of a pair of a stepper motors 40. The stepper motors 40 turn threaded lead screws 44 which pass through corresponding vertically oriented openings 42 (which have corresponding internal threaded profile to the screws 44) in a mid-section 42 of the dental work device 18. Although not shown in FIG. 5a, the mid-section 42 comprises the longitudinally oriented openings 24a, 24b and 26 (i.e. that facilitate coupling to rails 23a, 23b and lead screw 28). In this manner, the stepper motors 40 can be simultaneously actuated (either in forward or reverse) for facilitating upward and downward movement in the Z plane. It will be understood that in an alternative embodiment, only one stepper motor and lead screw may be required for facilitating the movement in the Z plane. An alternative embodiments for facilitating movement in the Z plane is shown in FIG. 5b. According to this embodiment, an actuator in the form of one or more micro air pumps are used to extend and contract the length of the dental work device 18 so as to adjust the height of the attachment 17 relative to the tooth 16. As shown in FIG. 5b, a plurality of telescoping cylinders 46, 48, 50 have internal chambers that are connected by way of a series of valves. The cylinders 46, 48, 50 are caused to extend or retract relative to one another by applying pressure or suction to the chambers by way of the air pump(s). Although not shown in FIG. 5b, the upper most cylinder 46 comprises the longitudinally oriented openings 24a, 24b and 26 that facilitate coupling to rails 23a, 23b and lead screw 28. It will also be understood that the rails 23a, 23b and 32a, 32b (and corresponding openings 33, 38) may be of any desired cross sectional profile, depending on the desired implementation. Further, the rails 23a, 23b, 32a, 32b may be positioned at any desired height within the body 12, depending on the desired implementation. According to the illustrated embodiment, the dental work device 18 is adapted to move up to 2 cm in in Z plane.

Still with reference to FIGS. 5a and 5b, the attachment 17 is in the form of a bur that removably couples to the work device 18 by way of an actuator in the form of an air powered turbine 35 (e.g. by way of frictional, magnetic or latch fit). The attachment 17 couples to the work device 18 by way of a rotator 37 (in this embodiment taking the form of a pneumatic rotary actuator 37 which rotates the attachment 17 between 0 and 360 degrees as indicated by reference numeral D) and pivot mechanism 39 that in turn couples to the work device 18 by way of a pair of arms 41. A further actuator (in this illustrated embodiment being in the form of an air powered pneumatic motor 39) causes a pivot portion of the mechanism to pivot relative to the arms 41 (i.e. for moving between 0 to 180 degrees as indicated by reference numeral E). The rotator 37 and pivot mechanism 39 advantageously provide two additional planes of movement for performing the necessary work. It will be understood that some or all of the above described actuators/motors/engines for controlling movement in the X, Y and Z planes (as well as for rotating and pivoting the work attachment 17) could be electrically powered, air powered or electromagnetically powered, depending on the desired implementation.

Also shown in the figures is a conduit 30 that is connected to the body 12 and which, in use, facilitates the delivery or removal of fluid to/from the work site and/or dental work device 18. For example, the conduit 30 may deliver compressed air to the work site as required for the procedure. The compressed air may also be directed to any one or more air powered actuators utilised by the apparatus 10. The conduit 30 may additionally or alternatively deliver water (e.g. pressurised water) to the work site. In addition, or as an alternative, the conduit 30 may be used to suction air and/or water from the work site during the procedure. As yet another additional or alternative use, the conduit 30 may carry electrical and/or data cable for providing power and/or commands to any electrically powered actuators and/or circuitry provided by the apparatus 10. The conduit 30 may also carry all of the necessary control signals to/from the circuitry (e.g. image data captured from the cameras).

In a particular embodiment, the conduit 30 may be connected to a housing containing an extra-oral air compressor (for delivering the compressed air), a water chamber for supplying water, a suction pump and a receptacle used to store any substances received from the work site via the conduit. The conduit 30 may comprise separate tubes for carrying the various fluids and cables. In an alternate embodiment, the conduit 30 may be connected to pre-existing air, water and electricity outlets that may be within structures such as such as existing conventional dental chairs (dental units).

In an embodiment, one or more lights are disposed on the body 12 to illuminate the teeth 16 and/or surrounding oral cavity 13. In a particular embodiment an LED light is located at each internal corner of the body 12 (i.e. directed toward the work site). In addition, the apparatus 10 may be provided with a bore light or other such light for transillumination (e.g. disposed on an inner wall of the body). The apparatus 10 additionally comprises a camera 31 (again which may be disposed on an inner wall of the body 12 facing the work site) for capturing image data for the work site and surrounding area.

As shown in FIG. 1, the apparatus 10 is connected to a controller 20 for electrically controlling actuation of the various apparatus actuators and imaging devices to perform the desired dental procedure. For example, with regards to the air powered actuators, the controller is operable to control the air supply unit to deliver the necessary amount of air/suction for achieving the necessary movement. For electrical actuators, the controller 20 may directly deliver the necessary power or signal thereto via an electrical cable disposed in the conduit 30. Alternatively, the controller 20 may be configured to wirelessly communicate with the actuators, e.g. via Bluetooth, WiFi or the like. In a particular form, the controller 20 may comprise a microcontroller or other suitable processing system including a memory storing program code for automatically controlling the actuators (i.e. based on predefined instructions). Additionally, or alternatively, the controller 20 may include a user interface that allows an operator to manually control the actuators. This may be the case for dental procedures, such as drilling, where the operator may wish to manually control the angle and depth for drilling. The controller 20 may be configured to cause a display device to display relevant real time procedural information, including image data captured from the camera(s), as well as any other relevant information (including warnings, actuator feedback data, etc.). Thus, in one example, the controller 20 may include a wireless receiver configured to receive a remote control signal, for controlling the apparatus 10. In an alternative embodiment to that shown in the figures, the controller 20 may be embedded in or disposed on the body of apparatus 10 and can be programmed to wirelessly communicate with a remote control device. In yet another embodiment, the controller may be configured to connect to a remote network, such as the Internet, allowing the apparatus to be controlled remotely, for example as a means of urgent dental intervention, where dentists are not readily accessible such as in extremely remote areas (e.g. outer space) or those suffering conflicts or natural disasters. The apparatus 10 might be attended in site by a dental assistant or nurse or a person trained for this purpose, and operated remotely by a dentist from abroad.

Examples of Work Performed by Apparatus:

Imaging

In a particular embodiment, the camera 31 is able to capture image data (corresponding to images of the work site or oral cavity) that can be processed by the controller 20, e.g. for creating a three-dimensional model of the work site. The model can, for example, be referenced by the programs stored in the controller memory for use in determining how to implement a particular dental procedure. The model can also be stored for future evaluation (e.g. to monitor a particular condition, treatment, etc.). Alternatively, or additionally, the controller 20 may be programmed to accept a scanned model of the work place generated by a standalone intra-oral scanner.

The controller 20 may further be configured to display the image data on a display device, thereby allowing a practitioner to examine the tooth or teeth within the work site (i.e. obviating the need for an additional standalone intra oral camera or magnifier). For example, the image data may allow a practitioner to clearly identify the location, type and size of an anomaly and as a result suitably prepare for treatment. Additionally, after completion of cavity preparation, a three-dimensional cavity filler can be produced based on the information obtained from the one or more cameras.

The camera(s) 31 may be fitted with a zoom functionality to allow a close and detailed inspection of the work site, which can aid in diagnosing dental ailments. In some instances, a microscopic lens can be added to the camera. Further, the information captured by the one or more cameras can allow a spatial relationship between the tooth and the apparatus 10 to be established. This special relationship informs the controller 20 of where the tooth or teeth are to thereby ensure that the work is performed with a high degree of accuracy.

In a particular embodiment, a practitioner can compare image data from the work site prior to and after treatment. For instance, the before image data may be overlayed with an image of the treated site. A person skilled in the art will appreciate that there are numerous methods to compare the before and after work site that do not depart from the invention.

A fluorescent light may be fitted to the apparatus which allows the camera(s) to detect fluorescence emission by microbes in dental plaque on the tooth. The resultant images that are obtained can be processed to detect caries which may be displayed on a screen in a different colour.

As previously stated, the apparatus 10 comprises a light suitable for transillumination (e.g. a bore light). In a particular embodiment, the controller 20 may turn on the light to highlight the structure of the tooth 16, which may also be used to identify caries, cavities or cracks in the tooth whether mesodistally or occlusally, as well as a range of other ailments. The camera 31 may be controlled to capture image data resulting from the transillumination which may be evaluated (e.g. manually or by the stored programs) to plan a treatment for any discovered ailments.

In other instances, the one or more lights coupled with one or more cameras allow for any drilling procedures that may be required to be evaluated, recorded and visualised. This is achieved as the one or more cameras are able to obtain the real-time dimensions and imagery of the tooth allowing the accurate location of where work must be performed on the tooth. A person skilled in the art would appreciate that a light fitted into the apparatus 10 is only one of the many ways the transillumination technique can be exploited by the apparatus. Alternatives include using a separate standalone transillumination device, such as an external light device, while also using the camera feature and/or drilling feature of the apparatus 10 to provide enhanced visualisation of the results.

Drilling and Tooth Preparation

In a particular embodiment, the attachment 17 comprises a bur drill. A specific example of a drill is shown in FIGS. 5a and 5b. As illustrated, the bur drill 17 attaches to the work device 18 by way of the rotator 37 and pivot mechanism 39. In one embodiment, the drill 17 is air powered by a rotary turbine engine 35 that can create a drill speed of up to approximately 200,000 revolutions per minute. It will be understood that the drill speed may be controlled automatically by the controller 20 or manually under the control of an operator (via a suitable controller interface). In an alternative embodiment, the engine 35 may be an electrically powered engine, or other suitably powered engine for carrying out the work. It will also be understood that various shaped and sized burs may be attached by the operator to the work device 18, depending on the desired implementation using bur drill attachments that are well understood in the art.

Fillings and Crowns

Figure 6:
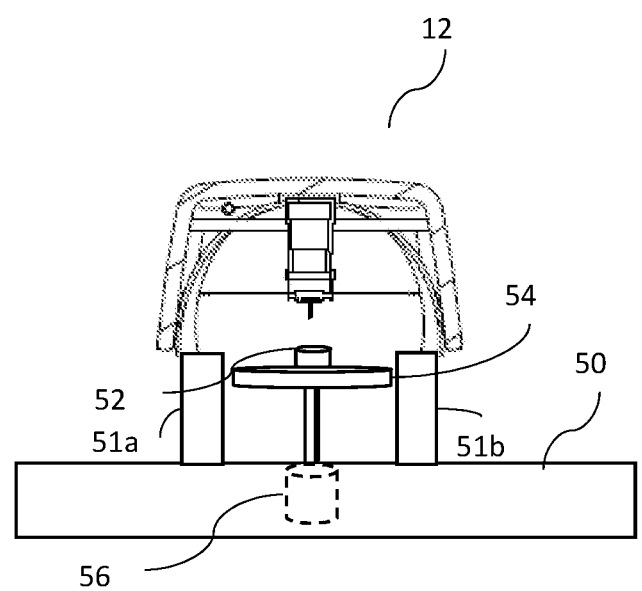
FIG. 6 is a schematic of the apparatus attached to an extra oral base for carving a filling.

In an embodiment of the present invention, the apparatus 10 is also able to create fillings and crowns. As an initial step, the apparatus 10 creates a three dimensional model of the subject tooth using techniques as hereinbefore described. This can be achieved through the camera and history of the drilling, or using a commercially available intraoral standalone scanning device. The controller can use the fluorescence result, the dentist's demarcation through the mouse/joystick and his choice of a certain cavity type and dimensions to design a digital cavity. Then, the body 12 of the apparatus 10 is detached from the tooth 16 and re-attached to a specialised extraoral base 50, as shown in FIG. 6. According to the illustrated embodiment, the bows of the clamp are respectively inserted into slots disposed in a pair of arms 51a, 51b that extend from base 50, so as to secure the body thereto. It will be understood that the body 12 could be attached to the base using any suitable securing technique (e.g. the bows could clamp over the arms 51a, 51b in the same way they clamp to the tooth 16). In yet another embodiment, the body 12 could be detached from the clamp 14 and re-attached to the base 50 using an alternative securing means. A prefabricated block of filling material 52 is secured by the operator to a cradle 54 coupled to an internally housed rotator 56 that can be controlled by the controller 20. The cradle 54 may also be moveable in other planes (e.g. using a similar mechanism to that used for moving the dental work device), depending on the desired implementation. The controller 20 then controls the various actuators to carve the material 52 to conform to the cavity and thus produces the desired crown or filling that fits the prepared tooth. The dentist then cements this structure using dental cements. It will be understood that the base 50 may include its own water and power supply, depending on the desired implementation.

Other Aspects

Different embodiments of the apparatus 10 may be created to perform one or more of the following dental procedures: root canal therapy, implant placement, surgical sectioning and extraction, periodontal therapy and soft tissue surgery, delivering local anaesthesia and the application and maintenance of orthodontic appliances. As previously stated, the body 12 of the apparatus 10 is adapted to be received within a patient's oral cavity 13. The size of the body may vary based on the type of oral cavity 13 that it is intended to perform dental procedures within. For instance, a lager sized body 12 may be used for an adult's oral cavity, while a smaller apparatus 10 may be used for a child's oral cavity. Persons skilled in the art will appreciate that the apparatus 10 as described herein can be used with animals, and as such the size of the device may be larger or smaller depending on the type of animal, and the type of teeth that will be treated. By way of example, the body 12 of an apparatus 10 for use with a human adult may be 3 cm×3 cm×2.3 cm (allowing it to be received wholly within the oral cavity) but should not be seen as being limited to this size, and may be bigger or smaller.

The apparatus 12 may also be fitted with a safety sensor that causes the controller 20 to cease work in response to detecting a hazard. By way of example, a pressure sensor may be fitted to an upper surface of the body 12. If a patient bites down on the apparatus 10, the pressure sensor will detect the bite and cause a signal to be sent to the controller 20 which causes the controller 20 to initiate an emergency procedure including ceasing operation of the actuators and raising the dental work device 18 off the tooth.

As hereinbefore described, the anchoring means 14 took the form of a clamp having a pair of bows. It will be understood that the body 12 may be configured to attach to any form of clamp depending on the desired implementation. For example, as persons skilled in the art will appreciate, that there are many forms of clamp having varied configurations that are suited to the working site (e.g. that conform to the different morphologies of teeth, such as anterior, posterior, upper and lower) and a dentists preferences. By way of example, the apparatus 10 could be removably attached to a wingless clamp, a distal clamp, a cervical or labial clamp, a retention clamp, a retraction clamp, or the like. Further, it will be understood that the body 12 may only secure to a single bow of the clamp.

In another anchoring embodiment, the body 12 may need to be anchored to more than one tooth simultaneously using more than one clamp. For example, one form of clamp may attach to two teeth (anterior and posterior) in operation. This is useful when the a particular tooth is badly broken down so that it is unable to receive clamping, or when there is a need to relieve the tooth of clamping and hence use adjacent teeth for apparatus retention.

The apparatus 10 is adapted to perform work within at least one work site. The work site is the portion of the oral cavity that requires diagnosis or treatment. In some instances, this may be the entire upper or lower arch, whereas in other instances this may only be a portion of the oral cavity, such as one or more teeth, a portion of the gingiva, or a combination of the two. There may be one or more work sites where the apparatus 10 is able to perform work. Work may be performed on these work sites at the same time, or at different times.

Persons skilled in the art will appreciate that the body and internal components may be formed of any suitable material that can be sterilized, such as alloy stainless steel. It will also be appreciated that any moving parts (such as motor gears used in the engines) are formed of a corrosion resistant material. An appropriate sterilization technique that may be employed includes placing the apparatus 10 in a steriliser, immersion or spaying with disinfecting solutions or the like.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The preceding description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In addition, the foregoing describes only some embodiments of the inventions, and alterations, modifications, additions and/or changes can be made thereto without departing from the scope and spirit of the disclosed embodiments, the embodiments being illustrative and not restrictive.

Furthermore, the inventions have described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the inventions. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment.

The invention claimed is:

1. An apparatus assisting in dental procedures, comprising:
    a first clamp comprising a pair of opposing clamp beaks that, in use, are adapted to secure to a crown of one or more teeth adjacent to gingiva in a first region of an oral cavity;
    a body detachably coupled to the secured first clamp and configured to be received within the oral cavity above the one or more clamped teeth, the body comprising an internal housing;
    a dental work device locatable in the internal housing such that the dental work device is positioned immediately above the one or more clamped teeth;
    a movement arrangement located in the internal housing and configured to adjust movement of the dental work device in a plurality of planes relative to the one or more clamped teeth so as to allow the dental work device to face different surfaces of the one or more underlying clamped teeth, the movement arrangement comprising a first motor for controlling movement of the dental work device along a first linear rail aligned with a first one of the plurality of planes and second motor for controlling movement of the dental work device along a second linear rail aligned with a second one of the plurality of planes, the first and second linear rails and correspondingly aligned planes being orthogonally disposed; and a controller for controlling the movement arrangement to suitably adjust the dental work device into position for performing the dental procedure and thereafter control the dental work device to carry out work on or about the one or more clamped teeth; and wherein, in an optional second use configuration, the body is configured to be detachably coupled to a second clamp that has a different structural configuration to the first clamp and which said different structural configuration allows the second clamp to secure to one or more teeth located in a different region of the oral cavity to the first region and wherein at least one of the first and second clamps is adapted for securing to one or more posterior teeth thereby allowing work to be performed thereon.

2. The apparatus of claim 1, wherein the work performed by the dental work device includes at least one pre-programed procedure.

3. The apparatus of claim 2, wherein the body comprises one or more cameras operable to take an image of a work site and wherein the controller is configured to process the resultant image data for use in determining at least one of:
 a. an adjustment to be made by the movement arrangement;
 b. appropriate selection of a preprogramed procedure;
 c. monitor in real time an operations performed by the apparatus; and
 d. diagnose anomalies in tooth structures by means of direct imagery, transillumination and/or fluorescence.

4. The apparatus of claim 1, wherein the first and second clamps each comprise one or more clamp bows extending from the beaks and wherein the body is detachably coupled to the bow(s).

5. The apparatus of claim 1, wherein the controller comprises a processing unit programmed to control the dental work device to perform the work.

6. The apparatus of claim 1, wherein the apparatus further comprises a conduit for supplying or expelling contents to/from the work device, the contents comprising at least one of fluids, gases or solids.

7. The apparatus of claim 1, wherein the dental work device comprises at least one of: a mechanical bur, forceps, root elevators, scalpel, a mirror, a laser, a camera, an excavator, a dental burnisher, a dental plugger, a scaler, local anaesthetic vehicle, and curette.

8. The apparatus of claim 1, wherein the work device moves along the rails by way of a threaded rod arrangement.

9. The apparatus of claim 8, wherein the first and second motors can be either air, water, steam or electrically powered under the control of the controller.

* * * * *